United States Patent
Takahashi (10) Patent No.: US 10,722,733 B2
(45) Date of Patent: Jul. 28, 2020

(54) POSITIONING APPARATUS AND METHOD OF POSITIONING

(71) Applicant: SHIMADZU CORPORATION, Kyoto-shi, Kyoto (JP)

(72) Inventor: Wataru Takahashi, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 263 days.

(21) Appl. No.: 15/473,803

(22) Filed: Mar. 30, 2017

(65) Prior Publication Data

US 2017/0291042 A1    Oct. 12, 2017

(30) Foreign Application Priority Data

Apr. 12, 2016    (JP) ................................ 2016-079445

(51) Int. Cl.
*A61N 5/10*    (2006.01)
*A61B 6/03*    (2006.01)
(Continued)

(52) U.S. Cl.
CPC ............ *A61N 5/1049* (2013.01); *A61B 6/032* (2013.01); *A61B 6/04* (2013.01); *A61B 6/0407* (2013.01);
(Continued)

(58) Field of Classification Search
CPC ........ A61N 5/10; A61N 5/103; A61N 5/1031; A61N 5/1048; A61N 5/1049;
(Continued)

(56) References Cited

U.S. PATENT DOCUMENTS 5,740,225 A * 4/1998 Nabatame ............... A61N 5/103
378/65
5,825,845 A * 10/1998 Blair .................... A61N 5/1049
378/62
(Continued)

FOREIGN PATENT DOCUMENTS

JP    2010-57810    3/2010
JP    2010-246733    11/2010
(Continued)

OTHER PUBLICATIONS

JP 2016-079445, Notice of Reasons for Refusal, dated Jun. 5, 2019, 5 pages—English, 5 pages—Japanese.

*Primary Examiner* — Allen C. Ho
(74) *Attorney, Agent, or Firm* — Andrew F. Young, Esq.; Lackenbach Siegel, LLP (57) ABSTRACT

A positioning apparatus and a positioning method has a control element and function 40 includes a radiograph acquisition element 41 that acquires radiograph data detected by two radiography systems selected from a group consisting of a flat panel detector, a DRR (Digital Reconstructed Radiograph) generation element 42 that generates DRR in two different directions by virtually performing fluoroscopic projection relative to the 3-dimensional CT data obtained through the network 17, a positioning element 43 that positions a CT to the X-ray fluoroscopic radiograph obtained from two radiography systems, and a displacement distance calculation element 44 that calculates a displacement distance of the tabletop 31 based on the gap between radiographs for improved positioning. The positioning element 43 has a multidimensional optimization element 45 and a 1-dimensional optimization element 46 that optimize parameters relative to rotation and translation of the fluoroscopic projection to maximize an evaluation function that
(Continued)

evaluates a matching degree between the DRR and the X-ray fluoroscopic radiograph.

1 Claim, 9 Drawing Sheets

(51) Int. Cl.
*A61B 6/04* (2006.01)
*A61B 6/00* (2006.01)

(52) U.S. Cl.
CPC .............. *A61B 6/40* (2013.01); *A61B 6/4007* (2013.01); *A61B 6/4014* (2013.01); *A61B 6/52* (2013.01); *A61B 6/5205* (2013.01); *A61B 6/5211* (2013.01); *A61B 6/5229* (2013.01); *A61N 5/10* (2013.01); *A61N 5/103* (2013.01); *A61N 5/107* (2013.01); *A61N 5/1031* (2013.01); *A61N 5/1048* (2013.01); *A61N 2005/1061* (2013.01); *A61N 2005/1062* (2013.01)

(58) Field of Classification Search
CPC .... A61N 2005/1061; A61N 2005/1062; A61N 5/107; A61B 6/032; A61B 6/04; A61B 6/0407; A61B 6/0457; A61B 6/40; A61B 6/4007; A61B 6/4014; A61B 6/52; A61B 6/5205; A61B 6/5211; A61B 6/5229; A61B 6/5235
USPC ..................... 378/62, 65, 42, 20, 68–69, 205
See application file for complete search history.

(56) References Cited

U.S. PATENT DOCUMENTS

| | | | | |
|---|---|---|---|---|
| 5,901,199 | A * | 5/1999 | Murphy | A61B 6/08 378/65 |
| 6,516,046 | B1 * | 2/2003 | Fröhlich | A61B 6/04 378/205 |
| 6,549,645 | B1 * | 4/2003 | Oikawa | G06T 11/008 382/132 |
| 6,674,833 | B2 * | 1/2004 | Shahidi | A61B 90/36 378/4 |
| 6,714,810 | B2 * | 3/2004 | Grzeszczuk | A61B 90/36 600/427 |
| 6,865,253 | B2 * | 3/2005 | Blumhofer | A61B 6/547 378/205 |
| 6,889,695 | B2 * | 5/2005 | Pankratov | A61N 5/10 128/898 |
| 6,907,281 | B2 * | 6/2005 | Grzeszczuk | A61B 90/36 378/41 |
| 7,010,080 | B2 * | 3/2006 | Mitschke | A61B 6/12 378/15 |
| 7,072,435 | B2 * | 7/2006 | Metz | A61B 6/032 378/62 |
| 7,187,792 | B2 * | 3/2007 | Fu | A61N 5/1049 382/128 |
| 7,199,382 | B2 * | 4/2007 | Rigney | A61N 5/1049 250/373 |
| 7,231,076 | B2 * | 6/2007 | Fu | G06K 9/3233 378/4 |
| 7,260,426 | B2 * | 8/2007 | Schweikard | A61B 6/12 600/407 |
| 7,280,633 | B2 * | 10/2007 | Cheng | A61N 5/1049 378/117 |
| 7,302,033 | B2 * | 11/2007 | Carrano | A61B 6/022 378/41 |
| 7,315,636 | B2 * | 1/2008 | Kuduvalli | G06T 11/008 128/922 |
| 7,327,865 | B2 * | 2/2008 | Fu | G06K 9/32 378/28 |
| 7,330,578 | B2 * | 2/2008 | Wang | G06T 15/08 345/419 |
| 7,349,522 | B2 * | 3/2008 | Yan | A61B 5/0816 378/65 |
| 7,366,278 | B2 * | 4/2008 | Fu | G06T 11/008 345/419 |
| 7,426,318 | B2 * | 9/2008 | Fu | G06T 7/344 382/294 |
| 7,436,928 | B2 * | 10/2008 | Urano | A61N 5/1049 378/64 |
| 7,453,983 | B2 * | 11/2008 | Schildkraut | A61N 5/1049 378/205 |
| 7,453,984 | B2 * | 11/2008 | Chen | A61N 5/1049 378/65 |
| 7,522,779 | B2 * | 4/2009 | Fu | A61B 6/5235 278/54 |
| 7,532,705 | B2 * | 5/2009 | Yin | A61B 6/025 378/22 |
| 7,570,738 | B2 * | 8/2009 | Khamene | A61B 6/032 378/20 |
| 7,620,144 | B2 * | 11/2009 | Bodduluri | A61B 6/02 378/41 |
| 7,623,623 | B2 * | 11/2009 | Raanes | A61N 5/1049 378/205 |
| 7,653,226 | B2 * | 1/2010 | Gühring | G06T 15/08 382/128 |
| 7,672,429 | B2 * | 3/2010 | Urano | A61N 5/1049 378/65 |
| 7,684,647 | B2 * | 3/2010 | Fu | G06K 9/32 345/630 |
| 7,713,205 | B2 * | 5/2010 | Fu | A61B 8/08 600/437 |
| 7,806,589 | B2 * | 10/2010 | Tashman | A61B 5/1038 378/193 |
| 7,831,013 | B2 * | 11/2010 | Star-Lack | A61N 5/1049 378/23 |
| 7,831,073 | B2 * | 11/2010 | Fu | A61N 5/1049 382/128 |
| 7,835,500 | B2 * | 11/2010 | Fu | A61B 6/4458 128/922 |
| 7,889,902 | B2 * | 2/2011 | Zhang | G06T 15/08 345/502 |
| 7,894,649 | B2 * | 2/2011 | Fu | A61N 5/1049 382/128 |
| 8,077,936 | B2 * | 12/2011 | Wang | G06Q 50/22 382/128 |
| 8,086,004 | B2 * | 12/2011 | Kuduvalli | A61B 6/588 382/128 |
| 8,130,907 | B2 * | 3/2012 | Maurer, Jr. | A61B 6/12 378/65 |
| 8,147,139 | B2 * | 4/2012 | Papaioannou | A61B 6/04 378/195 |
| 8,295,435 | B2 * | 10/2012 | Wang | A61N 5/10 378/65 |
| 8,315,356 | B2 * | 11/2012 | Core | A61N 5/1049 378/205 |
| 8,391,955 | B2 * | 3/2013 | Erbel | A61B 6/025 600/425 |
| 8,417,318 | B2 * | 4/2013 | West | A61B 6/12 600/424 |
| 8,457,372 | B2 * | 6/2013 | Fu | A61N 5/1049 382/128 |
| 8,471,222 | B2 * | 6/2013 | Handa | G06K 9/00 250/491.1 |
| 8,483,358 | B2 * | 7/2013 | Allison | A61B 6/00 378/65 |
| 8,498,377 | B2 * | 7/2013 | Fadler | A61B 6/032 378/62 |
| 8,515,004 | B2 * | 8/2013 | Star-Lack | A61B 6/025 378/23 |
| 8,536,547 | B2 * | 9/2013 | Maurer, Jr. | A61N 5/1081 250/492.3 |
| 8,559,596 | B2 * | 10/2013 | Thomson | G06T 7/0014 378/65 |
| 8,693,634 | B2 * | 4/2014 | Ramamurthi | A61B 6/5247 378/98.11 |

(56) References Cited

U.S. PATENT DOCUMENTS

| | | | | |
|---|---|---|---|---|
| 8,693,763 | B2* | 4/2014 | Berlinger | A61N 5/103 382/152 |
| 8,792,613 | B2* | 7/2014 | Gardner | A61B 5/04021 378/65 |
| 8,824,630 | B2* | 9/2014 | Maurer, Jr. | G06F 19/3481 378/20 |
| 8,831,706 | B2* | 9/2014 | Fu | A61B 6/032 378/65 |
| 8,849,633 | B2* | 9/2014 | Core | G16H 50/50 703/6 |
| 8,861,672 | B2* | 10/2014 | Maltz | A61B 6/032 378/4 |
| 8,874,187 | B2* | 10/2014 | Thomson | A61B 6/037 378/62 |
| 8,917,813 | B2* | 12/2014 | Maurer, Jr. | A61N 5/10 378/65 |
| 8,965,096 | B2* | 2/2015 | Yamada | A61B 6/032 250/491.1 |
| 8,989,846 | B2* | 3/2015 | Kuduvalli | A61B 6/00 378/181 |
| 9,108,048 | B2* | 8/2015 | Maurer, Jr. | A61N 5/107 |
| 9,230,322 | B2* | 1/2016 | Hirai | G06T 7/0012 |
| 9,393,445 | B2* | 7/2016 | Yamada | A61N 5/1039 |
| 9,415,240 | B2* | 8/2016 | Jordan | A61B 6/4035 |
| 9,427,201 | B2* | 8/2016 | West | A61B 6/466 |
| 9,533,172 | B2* | 1/2017 | Sugiura | G06T 19/00 |
| 9,538,940 | B2* | 1/2017 | Tashman | A61B 6/5223 |
| 9,616,251 | B2* | 4/2017 | Filiberti | A61N 5/1075 |
| 9,672,640 | B2* | 6/2017 | Kleiner | A61B 6/032 |
| 9,675,818 | B2* | 6/2017 | Hirai | A61N 5/103 |
| 9,687,200 | B2* | 6/2017 | Maurer, Jr. | A61B 6/032 |
| 9,743,896 | B2* | 8/2017 | Averbuch | G06T 7/20 |
| 9,830,718 | B2* | 11/2017 | Hirai | G06T 11/008 |
| 9,861,834 | B2* | 1/2018 | Xing | A61N 5/1031 |
| 9,886,760 | B2* | 2/2018 | Liu | A61B 6/487 |
| 9,892,526 | B2* | 2/2018 | Hirai | G06T 11/003 |
| 9,919,164 | B2* | 3/2018 | Taguchi | G06T 11/008 |
| 9,949,709 | B2* | 4/2018 | Yi | A61B 6/461 |
| 9,968,321 | B2* | 5/2018 | Wikler | A61B 6/032 |
| 9,990,711 | B2* | 6/2018 | Lugosi | G06T 7/0012 |
| 10,016,625 | B2* | 7/2018 | Taguchi | G06K 9/3241 |
| 10,065,049 | B2* | 9/2018 | Lugosi | G06T 17/00 |
| 10,083,511 | B2* | 9/2018 | Baumgart | A61B 6/487 |
| 10,092,251 | B2* | 10/2018 | Virshup | A61B 6/032 |
| 10,143,431 | B2* | 12/2018 | Hirai | A61B 6/0407 |
| 10,272,265 | B2* | 4/2019 | Filiberti | A61N 5/1049 |
| 10,297,042 | B2* | 5/2019 | Berlinger | A61B 6/5235 |
| 10,413,752 | B2* | 9/2019 | Berlinger | A61N 5/1067 |
| 10,434,335 | B2* | 10/2019 | Takahashi | A61N 5/1049 |
| 10,478,148 | B2* | 11/2019 | Siewerdsen | A61B 6/584 |
| 10,631,778 | B2* | 4/2020 | Kleiner | A61B 6/037 |
| 2018/0280727 | A1 | 10/2018 | Takahashi et al. | |

FOREIGN PATENT DOCUMENTS

| | | |
|---|---|---|
| JP | 2013-99431 | 5/2013 |
| JP | 2016-059606 | 4/2016 |
| WO | WO 2014/155556 | 2/2014 |

\* cited by examiner

POSITIONING APPARATUS AND METHOD OF POSITIONING

CROSS REFERENCE TO RELATED APPLICATIONS

This application relates to, and claims priority from, JP 2016-079445 filed Apr. 12, 2016, the entire contents of which are incorporated herein by reference.

FIGURE SELECTED FOR PUBLICATION

FIG. 2

BACKGROUND OF THE INVENTION

Field of the Invention

The present invention relates to positioning apparatus to perform the positioning for a patient when a medical treatment is performed on the patient and a method of positioning therefor.

Description of the Related Art

The therapeutic radiation relative to a radiation therapy, in which the radiation including an X-ray, an electron beam, a corpuscular radiation and so forth is irradiated to the affected area of the patient, must be accurately irradiated to the affected area. In such radiation therapy, firstly, an X-ray CT (imaging) is performed and a radiation therapy protocol is set up. And when the therapy uses the radiation therapy apparatus, a virtual fluoroscopic projection relative to 3-dimensional image data collected by an X-ray CT apparatus is applied and then a DRR (Digital Reconstructed Radiograph) is generated.

Relative to a positioning apparatus that performs the positioning of the patient (subject), an optimization operation of the fluoroscopic projection parameters is executed so that an X-ray fluoroscopic radiograph of an affected area of the patient held by a fixing equipment on the therapy table (bed) of the radiation therapy apparatus and the periphery thereof and DRR can resemble each other at the highest degree. And the DRR is positioned to the X-ray fluoroscopic radiograph, so that the gap between the position on the radiation therapy for the patient and the position when the radiation therapy protocol is prepared can be calculated and the positional gap can be reflected onto a displacement distance of the therapeutic table (Patent Document 1 to Patent Document 4).

RELATED PRIOR ART DOCUMENTS

Patent Document

Patent Document 1: JP Patent Published 2010-57810
Patent Document 2: JP Patent Published 2010-246733
Patent Document 3: JP Patent Published 2013-99431
Patent Document 4: PCT International Publication No. WO2014/155556

ASPECTS AND SUMMARY OF THE INVENTION

Objects to be Solved

When an X-ray fluoroscopy is performed from two oblique directions (having a tilt angle) to the patient, referring to Patent Document 4, the source image distance (SID) gets longer compared to when the X-ray fluoroscopy from two true directions (horizontal direction and vertical direction) to the patient on the therapy table, referring to Patent Document 1 to Patent Document 3. In such way, when the SID is long, the processing of optimization operation to position the X-ray fluoroscopic radiography image, which is an actual image, and the DRR, which is a virtual projection image, slows down, and accordingly, the positioning takes a long time or additionally the degree of accuracy relative to the positioning therefor may be lessened.

Figure 7:
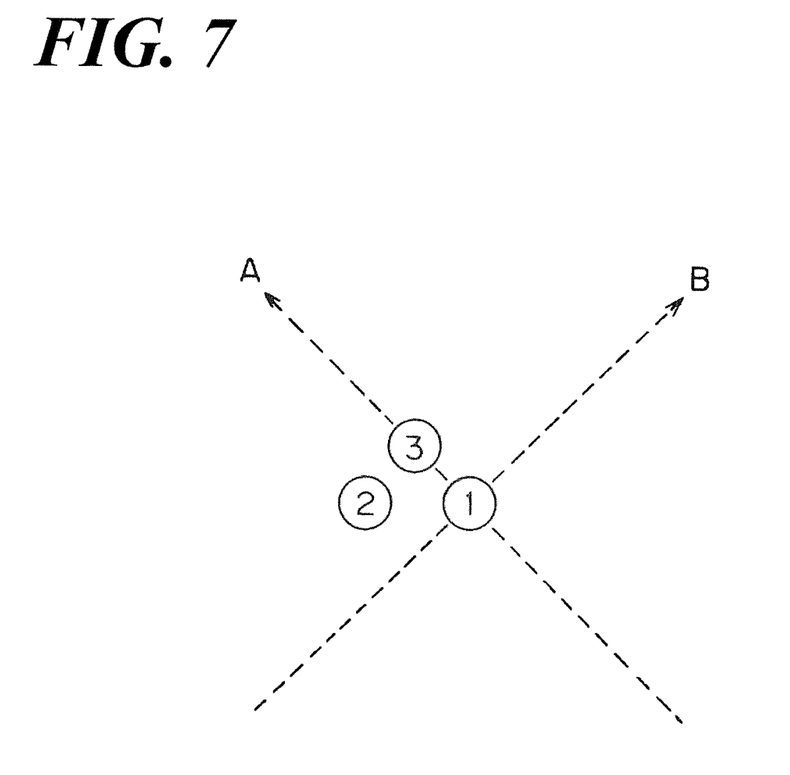
FIG. 7 is a schematic view illustrating X-ray fluoroscopic radiographs when the fluoroscopies are performed on the subject from two oblique directions.
Figure 8A:
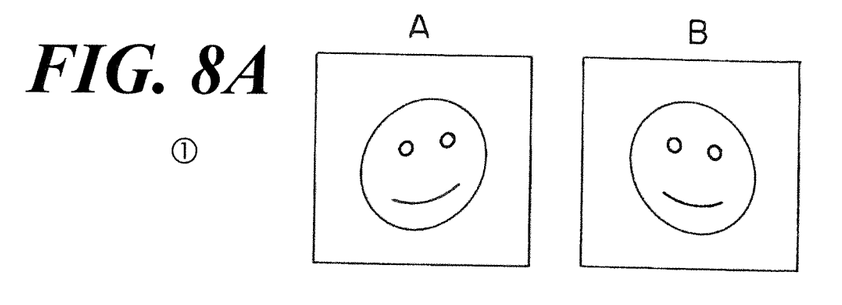
FIG. 8A, 8B, 8C are schematic views illustrating X-ray fluoroscopic radiographs when the fluoroscopies are performed on the subject from two oblique directions.
Figure 8B:
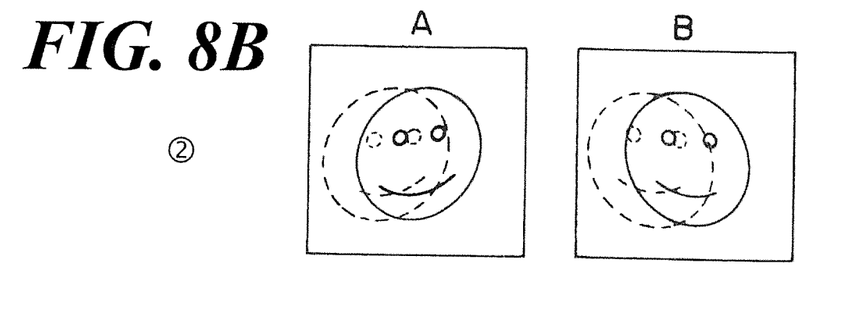
Figure 8C:
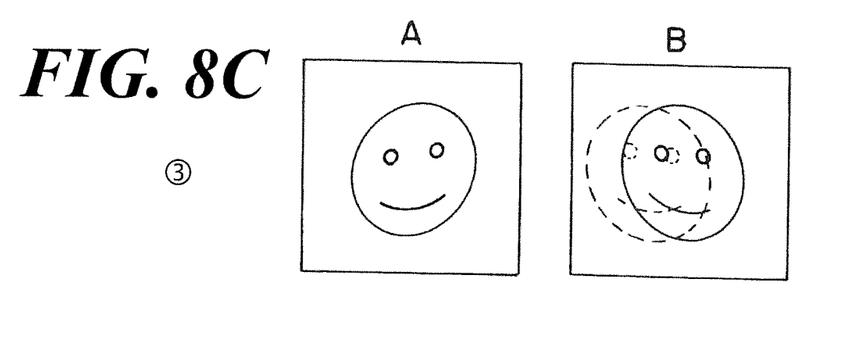

FIG. 7 and FIG. 8A, 8B, 8C are schematic views illustrating X-ray fluoroscopic radiographs when the fluoroscopies are performed on the subject from two oblique directions. FIG. 7 is illustrating the radiography direction and the position of the subject and FIG. 8A, 8B, 8C are illustrating the radiograph of which the DRR is superimposed to each X-ray fluoroscopic radiograph from the radiography direction A (indicated as radiograph A) and the radiography direction B (indicated as B) at each position indicated as 1, 2, 3 in FIG. 7. In addition, referring to FIG. 8A, 8B, 8C, the outline of the DRR is indicated by the solid line and the outline of the X-ray fluoroscopic radiograph is indicated by the broken line.

The positioning of the X-ray fluoroscopic radiograph and the DRR can be completed by solving an optimization problem that minimizes the search of the position at which the sum of the degree of similarity between radiographs from two directions is maximum as an object function (evaluation function), which is the opposite number of the sum of degree of similarity. When the position of the subject is indicated as the position 1 (referring to FIG. 7) which is an intersection point of the imaging directions A and B, no positional gap in both X-ray fluoroscopic radiograph and the DRR in the directions, A, B takes place (referring to FIG. 8A), so that the degree of similarity of radiographs can be high in any direction. Specifically, it is the condition in which the evaluation function value is a minimum. When the position of the subject is indicated as the position 2 (referring to FIG. 7) which shifts from both radiographing directions A and B, a positional gap in both X-ray fluoroscopic image and the DRR takes place in the directions A, B (referring to FIG. 8B), so that an additional optimization operation is continuously executed because the degree of similarity of images cannot be high in any direction.

On the other hand, when the position of the subject is indicated as the position 3 (referring to FIG. 7) which shifts along the direction A from the intersection point of both radiography directions A and B, no positional gap takes place between the X-ray fluoroscopic image in the direction A and the DRR, but instead a positional gap takes place between the X-ray fluoroscopic image in the direction B and DRR (referring to FIG. 8C). When SID is long, even if the subject moves along the radiography direction, the displacement variation is minor, so that the position of the X-ray fluoroscopic image and the position of the DRR in such direction match each other and in addition, each size of the subject can be almost the same. Accordingly, the degree of similarity of the image in the direction A is very high, so that the evaluation function value is very small even if the degree of similarity of the image in the direction B is not high. In such case, the processing of the optimization operation slows down. Such slowdown of the optimization operation is more obvious when the SID is long. Here, when consider the shape of the evaluation function, it is understandable that a valley structure in which the evaluation function value is extremely small is present. Then, the intersectional point of the two valleys along the two radiography directions is a global optimum solution (minimum value).

Figure 9:
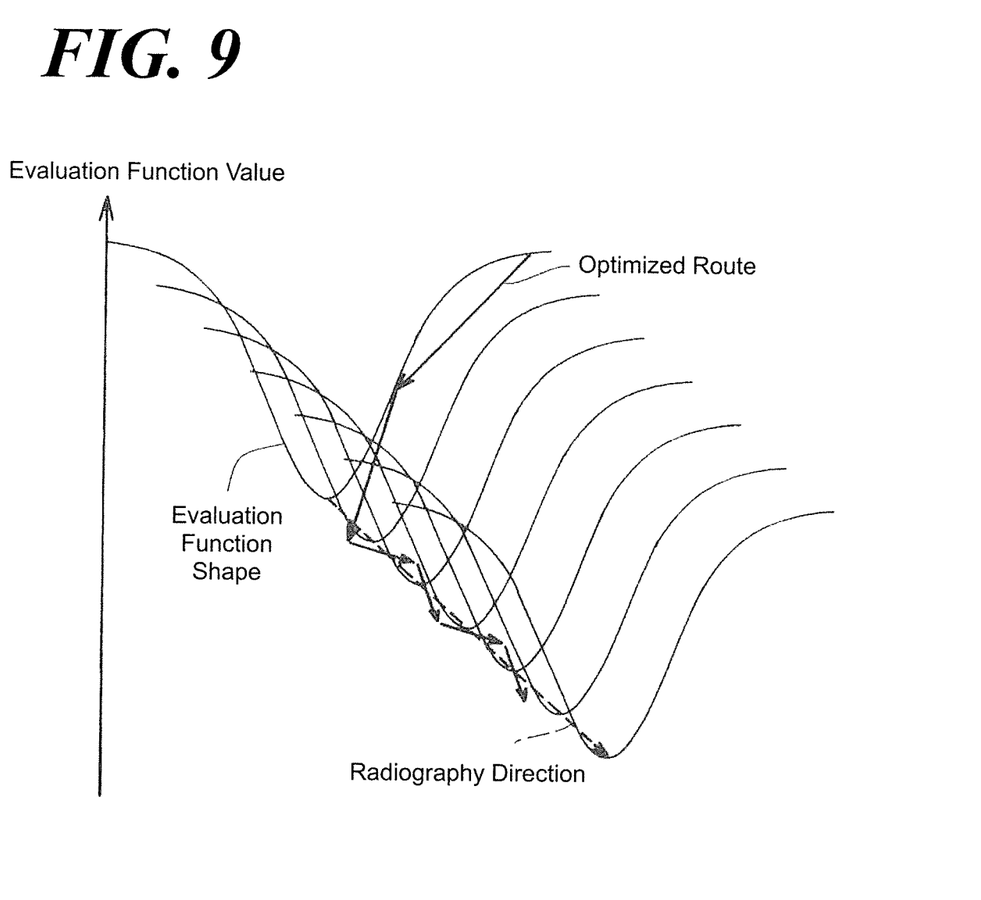
FIG. 9 is a schematic view illustrating an optimization process relative to the degree of similarity between the valley structure of the evaluation function and the conventional image.

FIG. 9 is a schematic view illustrating an optimization process relative to the degree of similarity between the valley structure of the evaluation function and the conventional image. Referring to FIG. 9, the radiography direction is indicated by the broken line arrow and the optimized route is indicated by the solid line arrow.

With regards to the optimization operation, when a plurality of valleys is present in the area (solution space) at which a solution is being obtained, a process in which a local optimum solution is being obtained based on the gradient of the evaluation function and a local optimum solution of the next valley is being obtained through the optimized route is repeated. Meantime, the optimization operation terminates when the defined time comes and when reached to the defined number of repetition so that the burden to the patient fixed on the therapy table would not increase. Accordingly, if the processing of the optimization operation terminates, a calculation to provide the global optimum solution cannot be accomplished.

When the subject is in the position along either side of the X-ray radiography direction A or B, the optimized route get often into the valley. The next traveling direction after gets into the valley is determined based on e.g., the gradient of the evaluation function and so forth without considering the radiography direction this time. Accordingly, since the next traveling direction is not along the valley structure, a slightly shifted direction would be calculated. And since the evaluation function value increases because of climbing the valley while traveling to the calculated direction, the traveling direction due to the next iteration would be calculated. Then, referring to FIG. 9, as the optimized route travels zigzag as crossing alternately the valley structure, the efficiency of optimization would worse. In such way, if the processing of the optimization operation slows down, the positioning of the subject takes a time and the optimum solution can be obtained within the designated time or by the calculation with the number of the designated repetitions, so that the degree of accuracy of positioning can be worsened.

Further, a variety of optimization methods are known, and e.g., when a conjugate direction method (Powell Method) is applied for optimization, the radiography direction can be designated to the initial optimized direction. In such case, the optimization can be executed at the initial optimization step while considering the radiography direction, but the optimized direction is updated by the iteration, the optimization considering the radiography direction allover aspect of the optimization operation may not be executed. In addition, when a gradient method including the method of steepest descent or the Newton Method is applied for optimization, the initial optimized direction is determined based on the gradient of the evaluation function, so that the radiography direction on optimization cannot be considered at all.

The purpose of the present invention is to solve the above objects and to provide a positioning apparatus and a positioning method that can improve the degree of accuracy of positioning for the subject.

Means for Solving the Problem

According to the first invention, a positioning apparatus that performs a positioning of a subject when the therapeutic beam is irradiated to an affected area of a patient on the therapy table is performed, comprising; a radiograph acquiring element that obtain a 2-dimensional radiograph in two different directions of a subject by a radiography system having a radiation irradiation element and a radiation detector; a DRR generation element that generates a DRR by the steps of reconstructing a geometric arrangement of an X-ray radiography system in a virtual space and performing virtually a fluoroscopic projection on X-ray CT data collected in advance; and a positioning element that positions the CT data and the radiograph so that an evaluation function is maximum to evaluate a matching degree between the radiograph in the two different directions and the DRR; wherein the positioning element further comprises: a multidimensional optimization element that optimizes parameters relative to rotation and translation corresponding to the moving axis of the therapy table in the fluoroscopic projection relative to the CT data; and 1-dimensional optimization element that optimizes parameters relative to 1-dimensional translation along the radiography direction of the radiography system.

According to an aspect of the second invention, the 1-dimensional optimization element determines whether to perform a 1-dimensional optimization or not based on the evaluation function value obtained by optimization by the multidimensional optimization element.

According to aspect of the third invention, the positioning element uses a different evaluation function between the multidimensional optimization element and the 1-dimensional optimization element.

According to an aspect of the fourth invention, the positioning element uses a different tolerance for convergence that determines convergence of optimization between the multidimensional optimization element and the 1-dimensional optimization element.

According to an aspect of the fifth invention, the positioning element performs a multiresolution processing that optimizes the radiograph in two different directions and the DRR by using the evaluation function that is different every resolution.

According to an aspect of the sixth invention, the positioning element determines whether or not the 1-dimensional optimization in the 1-dimensional optimization element should be performed every resolution.

According to an aspect of the seventh invention, a positioning method that performs a positioning for a subject when the therapeutic beam is irradiated to an affected area of a patient on the therapy table, comprises the steps of; obtaining a 2-dimensional radiograph in two different directions of the subject by a radiography system having a radiation irradiation element and a radiation detector; reconstructing a geometric arrangement of an X-ray radiography system in a virtual space and performing virtually a fluoroscopic projection on X-ray CT data collected in advance; and positioning CT data and the position of the radiograph so that an evaluation function is maximum to evaluate a matching degree between the radiograph in the two different directions and the DRR; and the positioning step further comprises: the steps of optimizing parameters in the multidimensional optimization step relative to rotation and translation corresponding to the movement axis of the therapy table in the fluoroscopic projection relative to the CT data; and optimizing parameters in 1-dimensional optimization step relative to 1-dimensional translation along the radiography direction of the radiography system.

Effect of the Invention

According to the aspects of the first invention to the seventh invention, the 1-dimensional optimization is performed to optimize parameters relative to 1-dimensional translation along the radiography direction of the radiography system, so that an efficient optimization operation can be performed considering the radiography direction when the shape of the evaluation function has a valley structure in which the evaluation function value is extremely small. In addition, the calculation time can be shortened and the degree of accuracy of positioning can be improved.

According to an aspect of the second invention, the 1-dimensional optimization element determines whether or not to perform 1-dimensional optimization based on the evaluation function value obtained by optimization by the multidimensional optimization element, so that the 1-dimensional optimization operation can be performed when e.g., a solution gets in the valley structure and then only when a contribution to the optimization can be expected, and the calculation time can be shortened.

According to aspect of the third invention, a different evaluation function between the multidimensional optimization and the 1-dimensional optimization is used, so that the positioning can be performed with a higher degree of accuracy.

According to the aspect of the fourth invention, a different tolerance is used for convergence that determines convergence of optimization between the multidimensional optimization and the 1-dimensional optimization, so that the positioning can be performed with the higher degree of accuracy.

According to an aspect of the fifth invention, the multi-resolution processing is executed; a matching degree to DRR generated by a low resolution is evaluated at the initial step of the optimization at which a position gap is large; the position gap gets smaller due to the repeated calculation; and the matching degree between images is evaluated by the high resolution image at a final step for optimization at which the positioning must be performed in the higher degree of accuracy; so that the optimization operation can be performed in a higher speed.

According to an aspect of the sixth invention, since it is determined whether the 1-dimensional optimization in the 1-dimensional optimization element should be performed every resolution or not, the 1-dimensional optimization can be skipped at the low resolution side at which an optimization direction in the solution space would not shift largely from the search direction for the preferred solution even without considering the radiography direction; so that the optimization operation can be performed in a higher speed.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Figure 1:
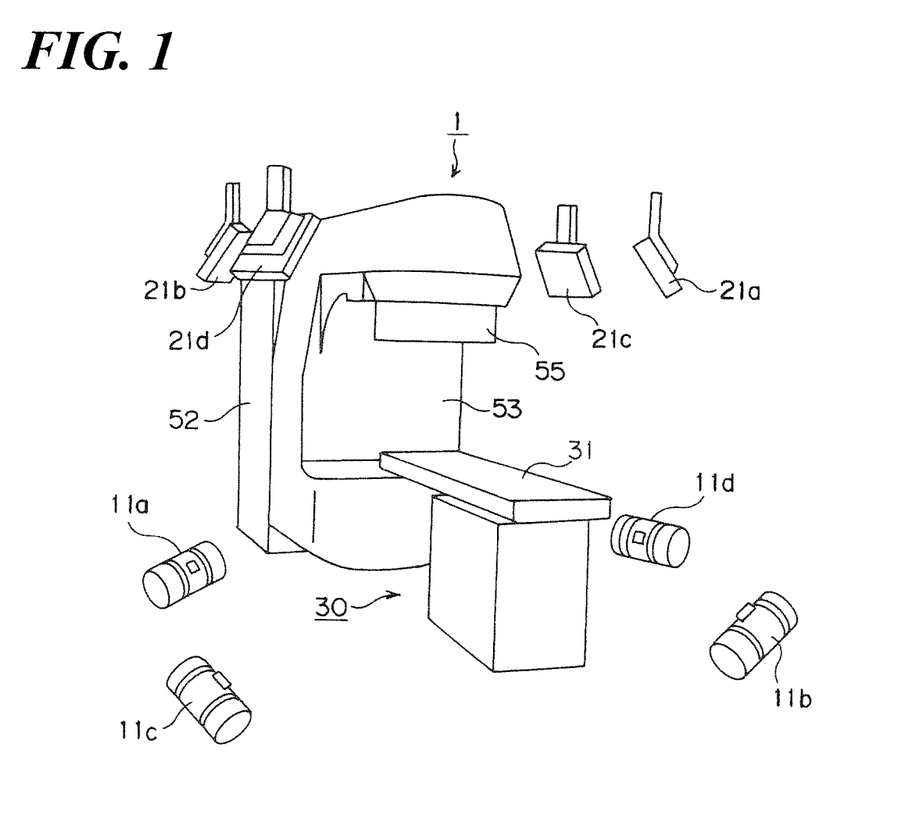
FIG. 1 is a schematic view illustrating a radiation therapy apparatus applying to a positioning apparatus to the aspect of the present invention.

The inventor sets forth Embodiments of the present invention based on the following FIGs. FIG. 1 is a schematic view illustrating a radiation therapy apparatus 1 including a positioning apparatus to the aspect of the present invention.

The positioning apparatus comprising an X-ray radiography system is used with a radiation therapy apparatus 1. The radiation therapy apparatus 1 that performs a radiation therapy for the patient (subject) on a tabletop 31 of a therapy table (imaging table) 30 comprises a head 55 that irradiates a therapeutic beam and a gantry 53 rotatably supported by the support column (base) 52 that is installed on the floor of a radiation therapy room. The radiation therapy apparatus 1 can change the irradiation direction of the therapeutic beam following the rotation of the gantry 53.

The X-ray radiography system performs an X-ray fluoroscopy to specify the affected area (position) of the supine patient on the tabletop 31 of the therapy table 30 comprises; X-ray tubes 11a, 11b, 11c, 11d that irradiate X-rays, and flat panel detectors 21a, 21b, 21c, 21d as X-ray detectors that detect an X-ray transmitted through the subject and the tabletop 31. The X-ray tubes 11a, 11b, 11c, 11d and the flat panel detectors 21a, 21b, 21c, 21d are in-place in the location at which an X-ray fluoroscopy can be performed on the subject in an oblique direction. In addition, even though it is not drawn in FIG. 1, the X-ray tubes 11a, 11b, 11c, 11d are in-place in concave areas formed on the floor and the concave areas are covered with a covering member as a part of the floor. In addition, an image intensifier (I. I.) can be applied to the radiation detector.

An X-ray irradiated from the X-ray tube 11a is detected by the flat panel detector 21a and the first radiography system comprises the X-ray tube 11a and the flat panel detector 21a. An X-ray irradiated from the X-ray tube 11b is detected by the flat panel detector 21b and the second radiography system comprises the X-ray tube 11b and the flat panel detector 21b. An X-ray irradiated from the X-ray tube 11c is detected by the flat panel detector 21c and the third radiography system comprises the X-ray tube 11c and the flat panel detector 21c. An X-ray irradiated from the X-ray tube 11d is detected by the flat panel detector 21d and the fourth radiography system comprises the X-ray tube 11d and the flat panel detector 21d. When positioning for the patient is performed, two selected radiography systems are selected from the group consisting of the first radiography system, the second radiography system, the third radiography system and the fourth radiography system and the fluoroscopies are performed on the subject from two different directions so that the gantry 53 cannot be overlapped in the radiography visual field.

Figure 2:
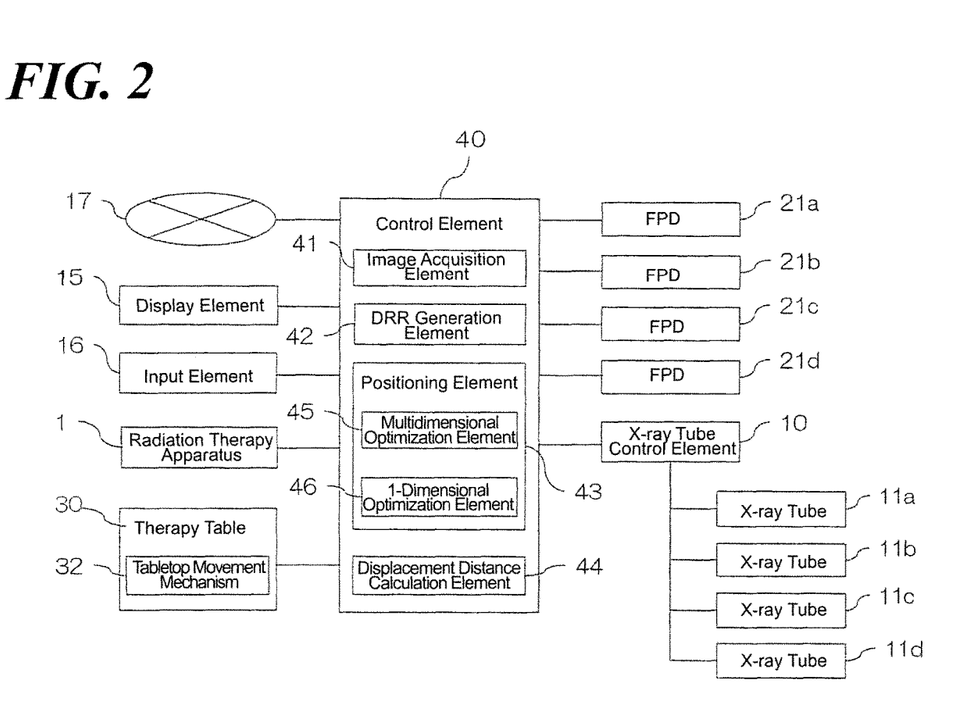
FIG. 2 is a block view illustrating a control system comprising the positioning apparatus according to the aspect of the present invention.

FIG. 2 is a block view illustrating a control system comprising the positioning apparatus according to the aspect of the present invention.

The positioning apparatus comprises a CPU (central processing unit) that executes a logical operation, a GPU (graphic processing unit) that executes a variety of image processings, a ROM that stores programs needed to control the apparatus, a RAM that temporarily stores data and so forth on executing the control, and a control element 40 that executes a positioning processing.

The control element 40 is connected to an X-ray tube control element 10 that controls an X-ray irradiation from the X-ray tubes 11a, 11b, 11c, 11d and to the flat panel detectors 21a, 21b, 21c, 21d. The X-ray tube control element 10 connected to the X-ray tube 11a, 11b, 11c, 11d supplies a tube voltage and a tube electric current to irradiate X-rays to two radiography systems selected from the group consisting of the X-ray tube 11a, 11b, 11c, and 11d on an X-ray fluoroscopy. In addition, the control element 40 is also connected to a network 17, a display element 15, an input element 16, the radiation therapy apparatus 1 and the therapeutic beam. In addition, the tabletop 31 of the therapy table 30 is movable and rotatable in 6 axes directions by the tabletop movement mechanism 32.

The control element 40 function-wise comprises a image acquisition element 41 that acquires the image data detected by two radiography systems selected from the group consisting of the flat panel detector 21a, 21b, 21c, and 21d, a DRR generation element 42 that generates DRR in the two different directions by virtually performing fluoroscopic projection relative to the 3-dimensional CT data obtained through the network 17, the positioning element 43 that positions a CT to the X-ray fluoroscopic radiograph obtained from two radiography systems, and a displacement distance calculation element 44 that calculates the displacement distance of the tabletop 31 from the gap between radiographs.

The positioning element 43 comprises a multidimensional optimization element 45 and a 1-dimensional optimization element 46 that optimize parameters relative to rotation and translation of the fluoroscopic projection so that the evaluation function that evaluates the matching degree between the DRR and the X-ray fluoroscopic radiograph can be maximum.

Figure 3:
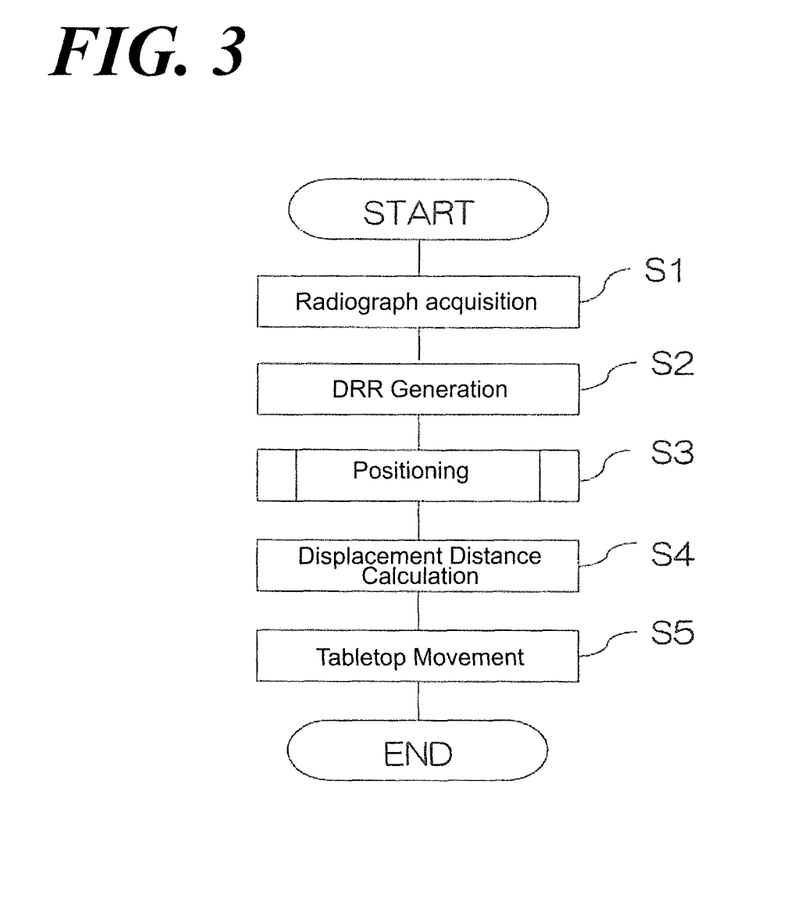
FIG. 3 is a flow-chart illustrating steps for positioning relative to a patient.

FIG. 3 is a flow-chart illustrating steps of positioning for the patient.

Radiograph data are obtained from two of the flat panel detector 21a, 21b, 21c, and 21d by performing an X-ray fluoroscopy with the selected two radiography systems relative to the patient on the tabletop 31 of the therapy table 30 and then an X-ray fluoroscopic radiograph in the two different directions (image acquisition step: Step S1).

A geometry of the X-ray fluoroscopic radiography is reconstructed in the virtual space on the computer, and a virtual fluoroscopic projection relative to a 3-dimensional CT data obtained in advance is executed. The CT data is obtained from the X-ray CT apparatus on the therapy protocol is prepared and stored in a patient database (not shown in FIG.). The control element 40 acquires the therapy protocol and the CT data through the network 17. And thereafter, a 2-dimensional DRR of the patient in the two different directions is generated by the virtual fluoroscopic projection to the CT data in the DRR generation element 42.

The geometry of the X-ray fluoroscopic radiography includes the positions of any two of the X-ray tube 11a, 11b, 11c, and 11d in two selected radiography systems, the positions of any two of the flat panel detectors 21a, 21b, 21c, and 21d, and the position/condition of the tabletop 31. The degree of mechanical installation accuracy of such elements effects on the degree of final positioning accuracy, so a regular correction of the installation position is performed and the correction result is reflected on the geometry of the X-ray fluoroscopic radiography.

When the DRR is generated (DRR Generation step S2), the voxel values of the CT data are integrated (line integral) along the projection line from any focal point of the X-ray tube 11a, 11b, 11c, and 11d to any flat panel detector of the flat detectors 21a, 21b, 21c, and 21d relative to the selected radiography system relative (refer to FIG. 12 of Patent Document 3).

The positioning element 43 optimizes parameters relative to rotation and translation so that the evaluation function, which evaluates the matching degree between the DRR and the X-ray fluoroscopic radiograph, can be maximum, and a positioning between the CT data and the X-ray fluoroscopic radiograph is executed (Positioning step S3). Here, normalized mutual information (NMI), gradient difference (GD), zero-means normalized cross-correlation (ZNCC) and so forth, which are conventionally being applied to positioning of the multimodality images, can be adopted. In addition, a combination of MI, GD, ZNCC can improve the degree of the evaluation relative to the matching degree between the DRR and the X-ray radiograph.

It is preferable that a calculation of the evaluation function is performed on only the area of the image at which the subject is radiographed. In addition, it is preferable that mobile organs and joints inside the subject, which are unreconstructable regions with the CT data, should not be a subject of the calculation of the evaluation function.

When the positioning element 43 completes the optimization operation of parameters and so forth, a displacement distance calculation element 44 converts the positional gap between the X-ray fluoroscopic radiograph obtained based on the positioning and CT data to the displacement distance of the tabletop (displacement distance calculation step: Step S4), and the displacement distance calculation element 44 sends such displacement distance to the tabletop movement mechanism 32 of the therapy table 30. Thereafter, the tabletop 31 moves following the operation of the tabletop movement mechanism 32 (table movement step: Step S5). In such way, the tabletop 31 is moved as much as the positional gap between the X-ray fluoroscopic radiograph and CT data, so that the subject is positioned in the position and at the angle as specified in the therapy protocol relative to the therapeutic beam irradiated from the radiation therapy apparatus 1. In addition, after the tabletop 31 is moved to position the subject, an X-ray fluoroscopy is performed again, and the X-ray fluoroscopic radiograph and DRR are displayed on the display element 15 so that a user can visually make sure whether both images are matching or not. And, the therapeutic beam is irradiated from the head 55 of the radiation therapy apparatus 1 to the affected area of the subject.

Figure 4:
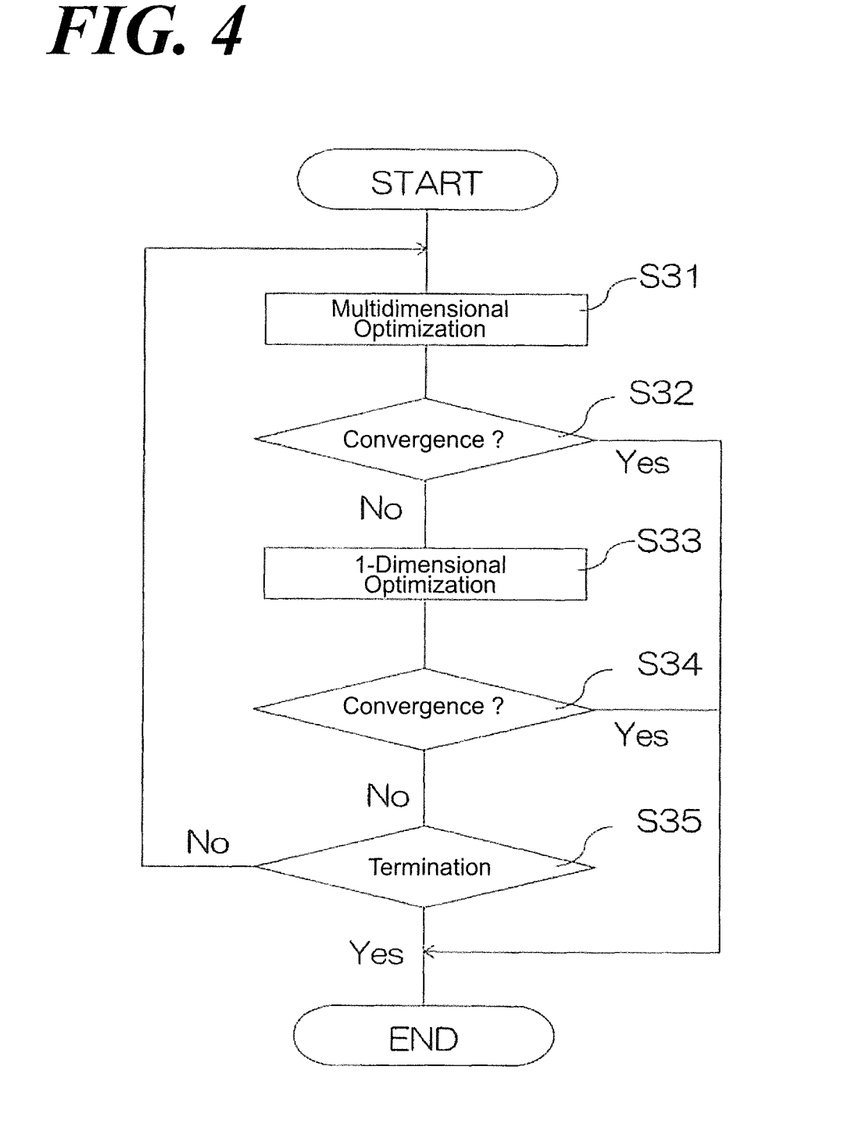
FIG. 4 is a flow-chart illustrating a procedure for an optimization of parameters.

The inventor sets forth further in detail relative to the optimization of parameters in the positioning element 43. FIG. 4 is a flow-chart illustrating a procedure for an optimization of parameters.

According to the aspect of the present Embodiment, since the therapy table 30 adopts the tabletop 31 corresponding to 6 axes movement, the evaluation function is a 6-dimensional function depending on 6 independent variables related to 3 rotation axes and 3 translation axes corresponding to the axes of movement of the tabletop 31. Accordingly, the target iso-center positioned in the irradiation field of the radiation therapy apparatus 1 is set as a rotational center, and a 6-dimensional optimization operation of the evaluation function is executed in the multidimensional optimization element 45 in the positioning element 43. In addition, the dimension of the multidimensional optimization element 45 is e.g., 4-dimension if the therapy table 30 moves the tabletop 31 in accordance with 4 axes movement.

Quasi-Newton method according to BFGS formula is applied to the method of the multidimensional optimization operation. According to the quasi-Newton method, if the evaluation function is f(x), the 6-dimensional position x is updated according to the following mathematical formula (1).

Mathematical Formula 1

$$x_{i+1} - x_i = H_{i+1}(\nabla f(x_{i+1}) - \nabla f(x_i)) \quad (1)$$

Here, H is an approximation of an inverse matrix of the Hessian matrix. In addition, some approximation formulae of H are proposed, but the BFGS formula according to the following mathematical formula (2), (3) can provide the best calculation efficiency.

Mathematical Formula 2

$$H_{i+1} = H_i + \frac{(x_{i+1} - x_i) \otimes (x_{i+1} - x_i)}{(x_{i+1} - x_i) \cdot (\nabla f_{i+1} - \nabla f_i)} - \frac{[H_i \cdot (\nabla f_{i+1} - \nabla f_i)] \otimes [H_i \cdot (\nabla f_{i+1} - \nabla f_i)]}{(\nabla f_{i+1} - \nabla f_i) \cdot H_i \cdot (\nabla f_{i+1} - \nabla f_i)} + [(\nabla f_{i+1} - \nabla f_i) \cdot H_i \cdot (\nabla f_{i+1} - \nabla f_i)] u \otimes u \quad (2)$$

Mathematical Formula 3

$$u \equiv \frac{(x_{i+1} - x_i)}{(x_{i+1} - x_i) \cdot (\nabla f_{i+1} - \nabla f_i)} - \frac{H_i \cdot (\nabla f_{i+1} - \nabla f_i)}{(\nabla f_{i+1} - \nabla f_i) \cdot H_i \cdot (\nabla f_{i+1} - \nabla f_i)} \quad (3)$$

Here, if the values of the evaluation function in the two different directions are F1, F2, then the sum, F1+F2, of the evaluation function in the two different directions is the final value of the evaluation function. In addition, when either one of the two different directions is more important relative to the positioning, a weighting addition relative to F1, F2 can be executed.

Parameters related to 1-dimensional translation along the radiography direction in the two selected radiography systems are optimized in the 1-dimensional optimization element 46 in the positioning element 43 (1-dimensional optimization final step: Step S33). The evaluation function in the 1-dimensional optimization element 46 is a linear function depending one variable related to the 1-dimensional translation along the radiography direction. Here, the Brent's method or the Golden Section method can be applied to such optimization.

As well as the multidimensional optimization, the final value of the evaluation function is the sum, F1+F2, of the evaluation functions in the two different directions if the values of the evaluation function in the two different directions are F1, F2, but it is preferable that only the evaluation function (either one of F1 or F2) having a large value is applied. Specifically, when the optimized route is along the valley structure of the evaluation function, the evaluation function having a small value is less contributive to the optimization, so if the optimization is performed using an object function having a large value in the side in which the positional gap is not along the radiography direction, such calculation is feasible in a high speed.

The multidimensional optimization (Step S31) and the 1-dimensional optimization are repeatedly performed until the evaluation function value reaches to the tolerance for convergence (determination step: Step S32, Step S34). In addition, if the evaluation function value could be determined as convergence after the multidimensional optimization (Step S32), the 1-dimensional optimization operation is skipped and the optimization operation ends. In addition, according to the aspect of the present Embodiment, different evaluation functions are used between the multidimensional optimization and the 1-dimensional optimization and different values for the tolerance for convergence of the value of the evaluation function are used. In such way, an adequate evaluation function and an adequate tolerance for convergence are respectively used, so that the optimization of parameters can be executed more adequately.

In addition, if the tolerance for convergence cannot be reached even when the predetermined calculation time is over or the predetermined calculation number is reached, the iterative counting for optimization is terminated (Termination determination step: Step S35). As such time limit is set, a burden to the patient who is fixed on the tabletop 31 under the constant body position and a decrease of the trough-puts of the radiation therapy apparatus 1 can be lessened. In addition, the multidimensional optimization operation and the 1-dimensional optimization operation are executed repeatedly relative to the optimization, so that the order of operation can be flipped.

Figure 5:
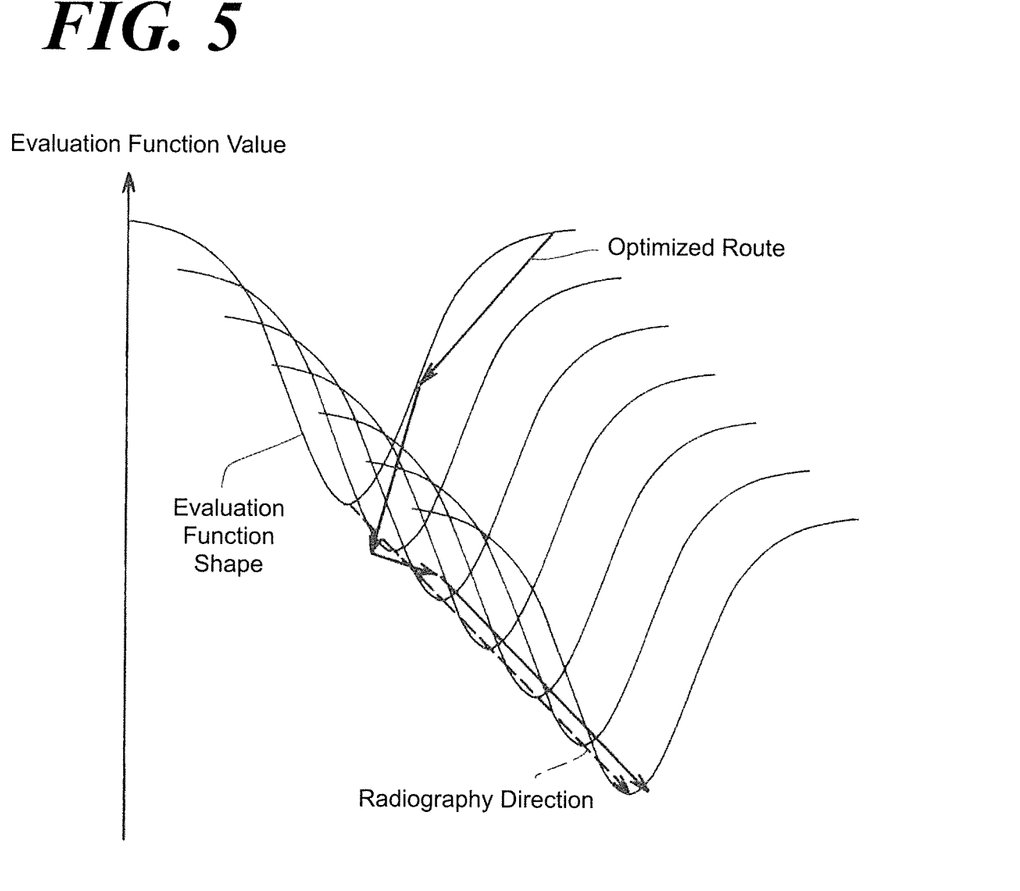
FIG. 5 is a schematic view illustrating an optimization process relative to the degree of similarity between the valley structure of the evaluation function and the radiograph when the 1-dimensional optimization operation according to the aspect of the present invention is executed.

FIG. 5 is a schematic view illustrating an optimization process relative to the degree of similarity between the valley structure of the evaluation function and the radiograph when the 1-dimensional optimization operation according to the aspect of the present invention is executed.

As 1-dimensional optimization element 46 optimizes parameters relative to the 1-dimensional translation along the radiography direction, the optimized route does not travel as if crossing conventionally the valley structure zigzag (referring to FIG. 9), but travels along the valley structurer referring to FIG. 5. Therefore, the optimization considering the radiography direction becomes feasible not only in the early stage but also in the end stage, so that the slowdown-concern of the processing of the optimization operation can be solved, in which SID gets longer when the X-ray fluoroscopy is conventionally performed on the subject in the two different oblique directions. Accordingly, since the optimization operation can be effectively executed, the total calculation time can be shorter than before and the degree of accuracy as for the positioning can be improved.

Figure 6:
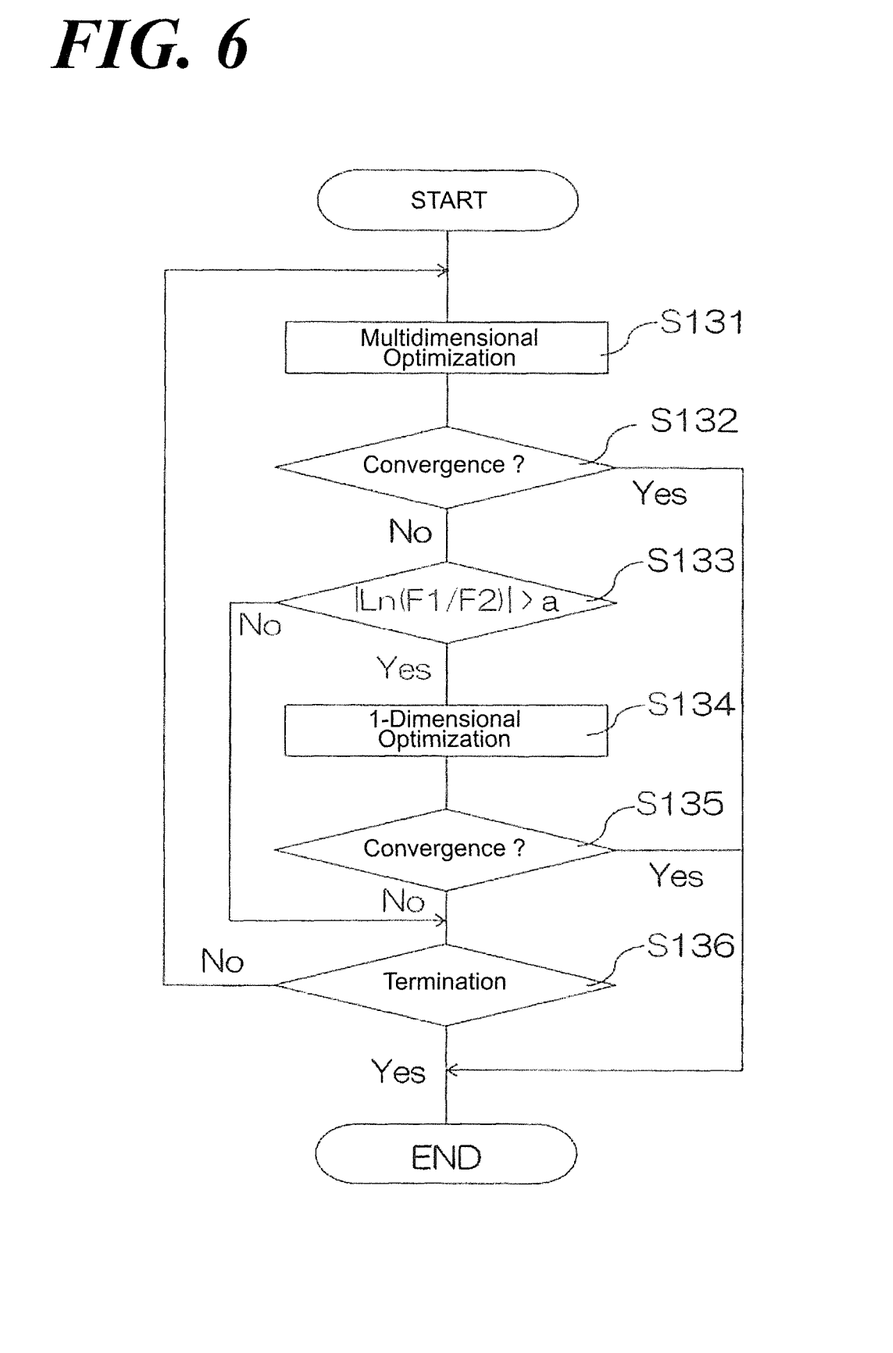
FIG. 6 is a flow-chart illustrating a procedure for an optimization of other parameters.

FIG. 6 is a flow-chart illustrating a procedure for an optimization of other parameters.

As well as the procedure referring to FIG. 4, the optimization procedure referring to FIG. 6 comprises: the steps of performing the multidimensional optimization (Step S131); determining the convergence of the evaluation function (Step S132); performing the 1-dimensional optimization (Step 134); determining the convergence of the evaluation function (Step S135); and determining the termination of the iterative counting for the optimization (Termination Step S136), but further comprises: the step of determining whether the 1-dimensional optimization should be executed prior to 1-dimensional optimization or not (Step S133), so that the procedure can be different from the procedure set forth before referring to FIG. 4.

It is preferable that if the values of the evaluation function in the two different directions just before 1-dimensional optimization are respectively F1, F2; the 1-dimensional optimization is executed only when an absolute value of Ln(F1/F2), representing a natural logarithm of F1/F2, is bigger than the predetermined value a. Specifically, it can be determined that the evaluation function is in the valley structure of the evaluation function (referring to FIG. 5 and FIG. 9) when the values of the evaluation function in the two different directions are very different each other. Specifically, the radiographs (images) in the two different directions are almost bilaterally symmetric (referring to FIG. 8), so that when in the valley structure, the difference between both values F1 and F2 can be big and when not, the difference can be small. Accordingly, only when the difference between both is big, the 1-dimensional optimization along the radiography direction can be executed. In such way, only when the value of the evaluation function gets in the valley structure, the 1-dimensional optimization is executed, so that the optimization can be executed out more efficiently.

In addition, the optimization operation of parameters can be executed in a high speed by combining the multiresolution processing with the optimization procedure set forth referring to FIG. 4, FIG. 5. Such multiresolution processing utilizes a downsampling method in which the multiresolution image has a pyramid structure of the X-ray fluoroscopic radiograph and the DRR and the X-ray fluoroscopic radiograph is specified as the low-resolution image by the downsampling in the initial stage of the optimization, at which the positional gap is large, and the matching degree with DRR generated in a low resolution is determined. And the matching degree between radiographs is evaluated by the high-resolution radiograph at the final step for optimization at which the positioning must be performed in the higher degree of accuracy because the positional gap gets smaller by the repetition calculation.

In addition, the higher resolution, the more frequent the evaluation function value trends to get in the valley structure, so when the multiresolution processing is executed every resolution, it can be switched whether the 1-dimensional optimization should be performed or not every resolution instead of repetition in which the multidimensional optimization and the 1-dimensional optimization are performed on all resolutions. Specifically, the 1-dimensional optimization can be skipped at the low-resolution side at which an optimization direction in the solution space would not shift largely from the search direction for the preferred solution even without considering the radiography direction, so that the optimization operation can be performed in a higher speed. In addition, it is preferable that the different tolerance for convergence is used every resolution based on the degree of accuracy obtained in each resolution when the multiresolution image processing is executed.

According to the positioning for the subject set forth above, the result of the positioning between the X-ray fluoroscopic radiograph and CT data in the positioning element 43 is utilized in the movement of the tabletop 31 prior to irradiation of the therapeutic beam from the radiation therapy apparatus 1, but the movement of the tabletop 31 is not mandatory. For example, the result of positioning can be utilized to make sure whether the positional gap takes place during the therapy. In addition, the dimension of the multidimensional optimization is e.g., 4-dimension if the therapy table 30 moves the tabletop 31 in accordance with 4 axes movement, but it is not always necessary that the dimension of the multidimensional optimization coincides with the displacement axis of the tabletop 31. For example, even though the tabletop 31 can take only 4 axes movement (3 axes translation and a vertical axis rotation), parameters for optimization can be 6-dimensional. In such case, 2 axes, not existing in the tabletop displacement axis, rotation is not available, but a warning display indicating that there is a positional gap of the 2 axes rotation can be displayed for the operator. The operator who realized the warning can conduct e.g., 2 axes rotation to position the patient's posture.

REFERENCE OF SIGNS

1 Radiation therapy apparatus
10 X-ray tube control element
11 X-ray tube
15 Display element
16 Input element
17 Network
21 Flat panel detector
30 Therapy table
31 Tabletop
32 Table movement mechanism
40 Control element
41 Image acquisition element
42 DRR generation element
43 Positioning element
44 Displacement distance calculation element
45 Multidimensional optimization element
46 1-Dimensional optimization element As used herein, a computer-based system includes an input device for receiving data, an output device for outputting data in tangible form (e.g. printing or displaying on a computer screen, sending data in the form of a value), optionally a permanent memory for storing data as well as computer code, and a microprocessor for executing computer code wherein said computer code resident in said permanent memory will physically cause said microprocessor to read-in data via said input device, process said data within said microprocessor and output said processed data via said output device.

It will be further understood by those of skill in the art that the apparatus and devices and the elements herein, without limitation, and including the sub components such as operational structures, circuits, elements, modules, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related diagnostic devices, computer and operational controls and technologies of radiographic devices and all their sub components, including various circuits and combinations of circuits without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm or process described in connection with the embodiments disclosed herein may be embodied directly in hardware, in a software module executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blue-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a web site. The website can be operated on a server computer, or operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A positioning method, that performs a positioning for a subject when a therapeutic beam of an X-ray radiography system is irradiated to an affected area of said subject on a therapy table, comprising the steps of:
    obtaining at least two 2-dimensional radiographs in two different radiography directions of said subject by said X-ray radiography system and at least two radiation detectors;
    generating at least two DRRs of said subject in the two different radiography directions by reconstructing a geometric arrangement of said X-ray radiography system in a virtual space and performing a virtual fluoroscopic projection on a set of CT data collected in advance; and positioning said set of CT data and said at least two 2-dimensional radiographs so that a first evaluation function that evaluates a matching degree between each of said at least two 2-dimensional radiographs in the two different radiography directions and said at least two DRRs has a first evaluation function value that is at a maximum, wherein said positioning step further comprises the steps of:

optimizing parameters in a multidimensional optimization step relative to a rotation and a translation corresponding to a moving axis of said therapy table in said virtual fluoroscopic projection of said set of CT data and relative to a 1-dimensional translation along the two different radiography directions of the X-ray radiography system; and     optimizing parameters in a 1-dimensional optimization step relative to the 1-dimensional translation along at least one of the two different radiography directions of said X-ray radiography system.

* * * * *